United States Patent
Wagenaar et al.

(10) Patent No.: US 6,838,672 B2
(45) Date of Patent: Jan. 4, 2005

(54) HIGH RESOLUTION, MULTIPLE DETECTOR TOMOGRAPHIC RADIONUCLIDE IMAGING BASED UPON SEPARATED RADIATION DETECTION ELEMENTS

(75) Inventors: Douglas J. Wagenaar, South Barrington, IL (US); John T. Pawlak, Lombard, IL (US); John C. Engdahl, Lake Forest, IL (US)

(73) Assignee: Siemens Medical Solutions USA, Malvern, PA (US)

( * ) Notice: Subject to any disclaimer, the term of this patent is extended or adjusted under 35 U.S.C. 154(b) by 0 days.

(21) Appl. No.: 10/015,779

(22) Filed: Dec. 17, 2001

(65) Prior Publication Data

US 2003/0111610 A1 Jun. 19, 2003

(51) Int. Cl.[7] .................................................. G01T 1/20
(52) U.S. Cl. ............................. 250/363.04; 250/363.1; 250/366

(58) Field of Search ........................ 250/363.04, 363.1, 250/366, 369

(56) References Cited

U.S. PATENT DOCUMENTS

| | | | | |
|---|---|---|---|---|
| 3,970,853 A | * | 7/1976 | Kuhl et al. ............. | 250/363.04 |
| 4,426,721 A | * | 1/1984 | Wang ..................... | 250/370.09 |
| 4,751,389 A | * | 6/1988 | Karcher et al. ........ | 250/363.04 |
| 5,144,141 A | * | 9/1992 | Rougeot et al. ............ | 250/369 |
| 5,453,623 A | * | 9/1995 | Wong et al. ........... | 250/363.03 |

* cited by examiner

Primary Examiner—Christopher W. Fulton (57) ABSTRACT

A radionuclide scanner in which multiple detectors are equipped with collimators such that a circular rotation of the detector around a target provides the movement needed for collimator sampling. This collimator sampling is accomplished through strategic placement of the detector heads relative to each other such that for any given projection, a complete imaging of the projection is acquired by summing the complementary contributions of the multiple detector heads at the projection under consideration.

15 Claims, 9 Drawing Sheets

(PRIOR ART)

HIGH RESOLUTION, MULTIPLE DETECTOR TOMOGRAPHIC RADIONUCLIDE IMAGING BASED UPON SEPARATED RADIATION DETECTION ELEMENTS

FIELD OF THE INVENTION

The present invention relates to an improved radionuclide imaging device having multiple collimated radiation detector elements for scanning three-dimensional targets.

BACKGROUND OF THE INVENTION

Radionuclide imaging devices, such as gamma cameras, are used in the medical field to measure radioactive emissions emanating from a subject's body and to form a comprehensible output from these measurements, typically in the form of an image that graphically illustrates the distribution of the emissions within the patient's body. The emissions originate from a decaying radioactive tracer that has been intentionally introduced into the subject's body, and therefore, the image produced by the radionuclide imaging device represents the distribution of the tracer within the subject's body. The radioactive tracer is a pharmaceutical compound to which an electromagnetic radiation emitting nuclide, such as $^{99m}$Tc, has been attached and which undergoes a physiological process after introduction into the body and exhibits an affinity for a certain organ or tissue.

The radionuclide imaging device has one or more detectors that detect the number of emissions, generally gamma rays in the range of 140 keV. Each of the detected emissions is a "count," and the detector determines the number of counts at different spatial positions. The imager then uses the count tallies to form an estimate of the distribution of the tracer, typically in the form of a graphical image having different colors or shadings that represent the count tallies.

Radionuclide imaging devices have traditionally used homogeneous area radiation detectors. For example, U.S. Pat. No. 3,011,057 for RADIATION IMAGE DEVICE, hereby incorporated by reference in its entirety, describes a radiation imager that uses a single NaI scintillation detector crystal to detect gamma ray emissions. The NaI radiation detector is generally characterized by spatial resolution and energy resolution performance that is substantially uniform across the relatively large area of the NaI detector crystal surface.

Figure 1:
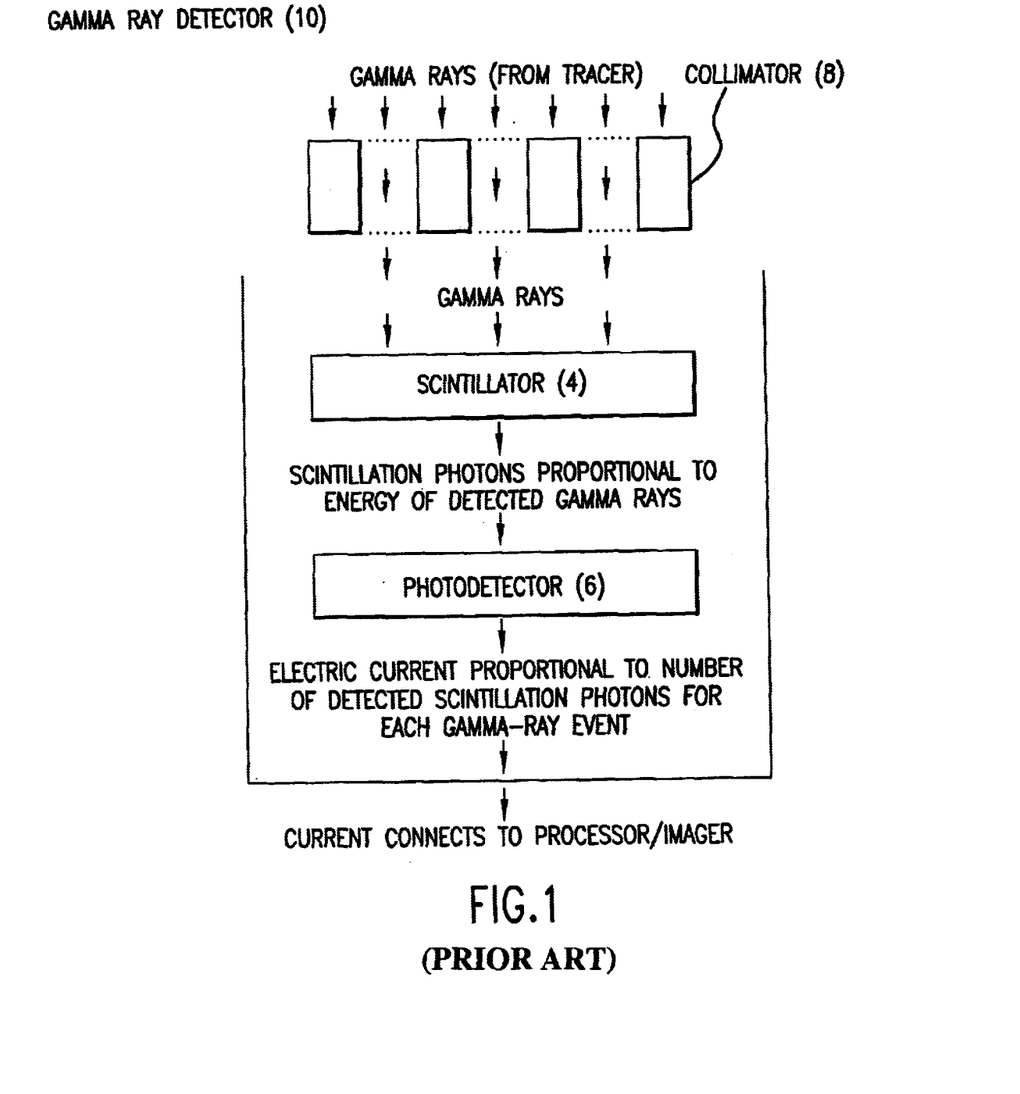
FIGS. 1 and 2 (PRIOR ART) are schematic illustrations of known radiation detectors.

FIG. 1 provides a schematic diagram of a traditional NaI radiation detector 10 that generally comprises a detector 4, such as a scintillation crystal, for transforming gamma ray emissions to light photons in response to incident gamma ray events, and a photodetector 6 to detect the light photons emitted from the scintillator. The photodetector 6, typically a photomultiplier tube that is optically coupled to the scintillator 4, detects a fraction of the scintillation photons produced from absorption of a gamma ray into the scintillation crystal and produces an electronic current that is proportional to the number of detected scintillation photons.

In one known technique used with NaI detectors, the radionuclide imager forms a high-resolution image through the use of a small-aperture collimator that provides collimated gamma ray paths to the detector. In this technique, the position of the gamma ray at the point of absorption in the scintillation crystal is determined by an algorithm based on the magnitude of electric signals from each of a plurality of photomultiplier tubes 6 positioned over the crystal. This algorithm can be implemented by use of a resistor matrix connecting the outputs of the photomultiplier tubes. For close proximity images, a single long-bore, small-aperture collimator hole can be used, with the collimator being scanned over the radiation field of interest in a two-dimensional scanning manner, to thereby sample radiation distribution over each of the image points in the radiation field. Multiple holes can be used to increase the number of counts obtained at each point, provided they are sufficiently separated from each other such that detected counts can be associated with a particular collimator hole.

For the radionuclide imager to form a high-resolution image, the detector must be able to distinguish between the photons received through each of the collimator holes. If the collimator holes are spaced too closely together, the spatial resolution advantage gained by using multiple collimator holes is lost because the intrinsic uniform spatial resolution and energy resolution of the NaI detector blurs the discernable location of a detected radiation emission such that detected radiation emission could have passed through any of several collimator holes. As a result, the density of the packing of the collimator holes is limited by distance of separation needed by the homogeneous NaI detector to achieve desired spatial resolution. This concept of separating multiple collimator holes by a sufficient distance to produce uniquely identifiable locations is known in the art and is described, inter alia, in U.S. Pat. Nos. 3,752,982 and 3,784,821, both issued to Jaszczak, and in International Application No. WO 00/38197 filed by Boxen, incorporated herein by reference. Because the collimator holes are sufficiently separated to allow the detector to identify the hole of origin for each detected radiation event, this imaging concept is henceforth referred to as the "sparse hole" technique.

The sparse hole imaging technique generally requires a precise motion of the collimator within a two-dimensional plane in order to obtain the usable counts needed to form images. This requirement for precise motion of the collimator throughout the sampling area adds considerable complexity to the design of the radionuclide imager. As a result, there exists a present need for a radionuclide imager having a relatively simple design that can move the collimator holes throughout a desired sampling area to obtain radiation counts while preserving the correct spacing necessary to produce high resolution images.

In addition to the above-described NaI detectors, radionuclide imagers with pixellated radiation detector elements, typically cadmium zinc telluride ("CZT") crystals, have recently been developed. In these pixellated radionuclide imagers, the intrinsic spatial resolution is defined by the size of the individual pixellated detector elements, rather than the separation between collimator holes. However, the pixel elements are nonhomogeneous in response and tend to have the best performance in the center of the pixel, with poorer performance at the boundaries between pixels. It can therefore be advantageous to have collimator holes allowing photons to interact with the centers of the pixels, where the collimator body masks the pixel-pixel boundaries. This idea of aligning the collimator holes with the centers of the pixels is henceforth referred to as the "registered collimator" concept and is analogous in operation to the above described sparse hole technique.

Figure 2:
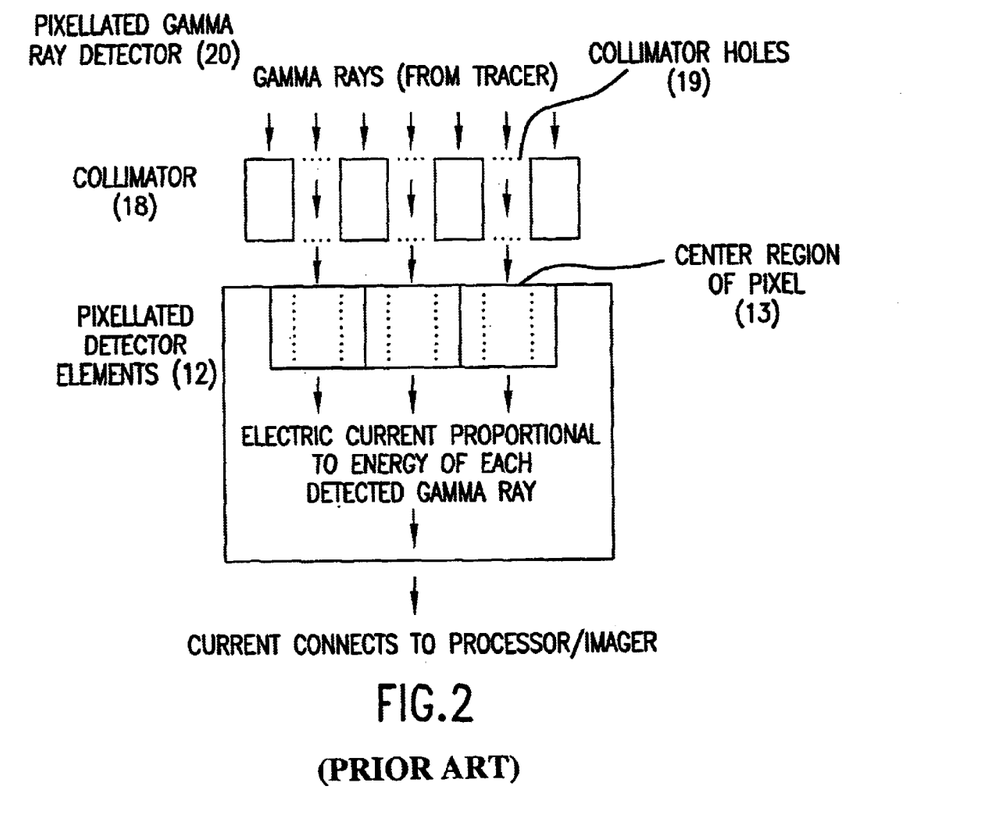

A typical pixellated radiation detector 20 is schematically illustrated in FIG. 2. The pixellated detector 20 is generally characterized by multiple detector elements 12. Each of the detector elements 12, as described above, has a center region 13 of higher detector performance. In order to direct radiation to the center regions 13 of the detector elements 12, the pixellated detector 20 further comprises a collimator 18 containing collimator holes 19 that correspond to the position of the individual detector elements 12.

Like the sparse hole imaging technique, registered collimator scanning generally requires a precise motion of the collimator holes within a two-dimensional plane in order to obtain the usable counts needed to form images, adding considerable complexity to the design of a radionuclide imager using pixellated detector elements. As a result, there exists a further need for a radionuclide imaging technique that can be adapted for use with registered collimator pixellated detector elements without adding complexity to the design and operation of the imager.

As described above, it is known in the field of radionuclide imaging devices to form imaging detectors by precisely positioning the collimated radiation detectors to scan a two-dimensional area by using either a sparse hole NaI detector or a pixellated CZT detector. In an imager having these types of multiple aperture, collimated detectors, the image resolution is ultimately limited by the definition of the collimator aperture in the individual detector elements. In particular, a detector element having a long bore, small diameter collimator aperture can produce superior spatial resolution, at the cost of reducing the number of gamma rays that are capable of traversing the aperture to be counted by the detector, thereby decreasing the sensitivity of the detector.

With radionuclide imagers having highly collimated detector elements, the spatial resolution performance rapidly degrades as distance increases between the detector's surface and the source of radiation. One cause for this degradation of spatial resolution is that the radiation emissions are not parallel and, as a result, become increasingly commingled as they move farther from the radiation source. Therefore, the radionuclide imager forms the best resolution images when the radiation sources are positioned in close proximity to the collimated detector elements. Accordingly, there exists a further need for a radionuclide imager that positions the collimated detectors in close proximity to the target to be scanned.

It is further known in the field of radionuclide imaging that the performance of the imager can be improved through the use of multiple radiation detectors. The use of multiple detectors is advantageous because the radionuclide imager may collect samples from a target in less time. An imager having two detectors, for instance, may scan a target twice as fast as an imager having a single detector. Furthermore, the use of multiple detectors to scan a target may improve the resolution of the scanning by reducing the variance and resulting statistical error produced by a single detector. However, configuring the multiple detectors for precisely scanning throughout a sampling area, such as required for sparse hole or registered collimator imaging, adds still greater complexity to the design for the radionuclide imager. As a result, there exists a further need for a radionuclide imager having multiple detectors and a relatively simple design.

Also, it has become increasingly important to perform high-resolution scanning of three-dimensional objects. For example, the accurate radionuclide imaging of small animals allows improved veterinarial diagnosis and superior results in scientific research. Likewise, the accurate radionuclide imaging of a body part, such as a breast, may aid doctors in providing more accurate medical diagnosis. While the NaI and CZT collimated radiation detectors are relatively simple, inexpensive devices that provide accurate, high-resolution count information from a planar sample area, these types of detector devices have not been adapted for use in scanning of three-dimensional targets. There accordingly exists a further need for a radionuclide imager that can scan and image three-dimensional objects using known high-resolution collimated radionuclide detectors.

SUMMARY OF THE INVENTION

These and other needs are addressed in the present invention through the use of multiple radionuclide detectors equipped with collimators such that a circular rotation of the detectors around the three-dimensional object to be imaged provides the movement needed for sparse hole or registered collimator sampling. A complete scan of the target is accomplished through strategic layout of the pixel array (for example, hexagonal close-packed or square array), and strategic placement of the detectors relative to each other such that for any given projection to be acquired, a complete high resolution scan is acquired by summing the complementary contributions from each of the multiple detectors when it is at that projection.

BRIEF DESCRIPTION OF THE DRAWINGS

The present invention is more fully described in the following attached drawings in which corresponding elements are designated by like reference numbers.

DETAILED DESCRIPTION OF THE PREFERRED EMBODIMENTS

The present invention provides an improved radionuclide imaging device having multiple radiation detectors for scanning three-dimensional targets. The present invention's radionuclide imager generally uses Single Photon Emission Computed Tomography (hereafter "SPECT") by rotating each detector around the target. In SPECT, the radiation detectors are rotated around the scanned subject to detect and count photon emissions from the radioactive tracer. When the detectors rotate around the scanned object, a lateral axis is defined as the mechanical axis of rotation aligned with a computer matrix for reconstructing the SPECT images. The radionuclide imager then uses the count value obtained by the rotating detectors to reconstruct the distribution of the radioactive tracer in the form of a cross-section image. The rotating detectors may be longitudinally moved relative to the scanned object in order to obtain multiple cross-section images. The multiple cross-section images may then be combined to form a three-dimensional image of the scanned object. For example, the acquisition of data for a total body scan requires movement of the detector along the length of the patient's body. Similarly, the acquisition of data for a scan of a body part, such as an arm, requires movement of the detector along the length of that body part.

In the present invention's radionuclide imager, a complete scan of the target is accomplished through a combination of strategic pixel array selection (e.g., square or close-packed hexagonal) and the strategic placement of the detectors relative to each other such that for any given projection to be acquired, a complete high resolution scan is acquired by summing the complementary contributions of the multiple detectors when each of the detectors is at that projection. This strategic positioning of the detectors during SPECT scanning is described below in greater detail. In this description of FIGS. 3–5, the axis of rotation is the vertical axis, and the tomographic slices acquired through SPECT are horizontal lines.

Figure 4:
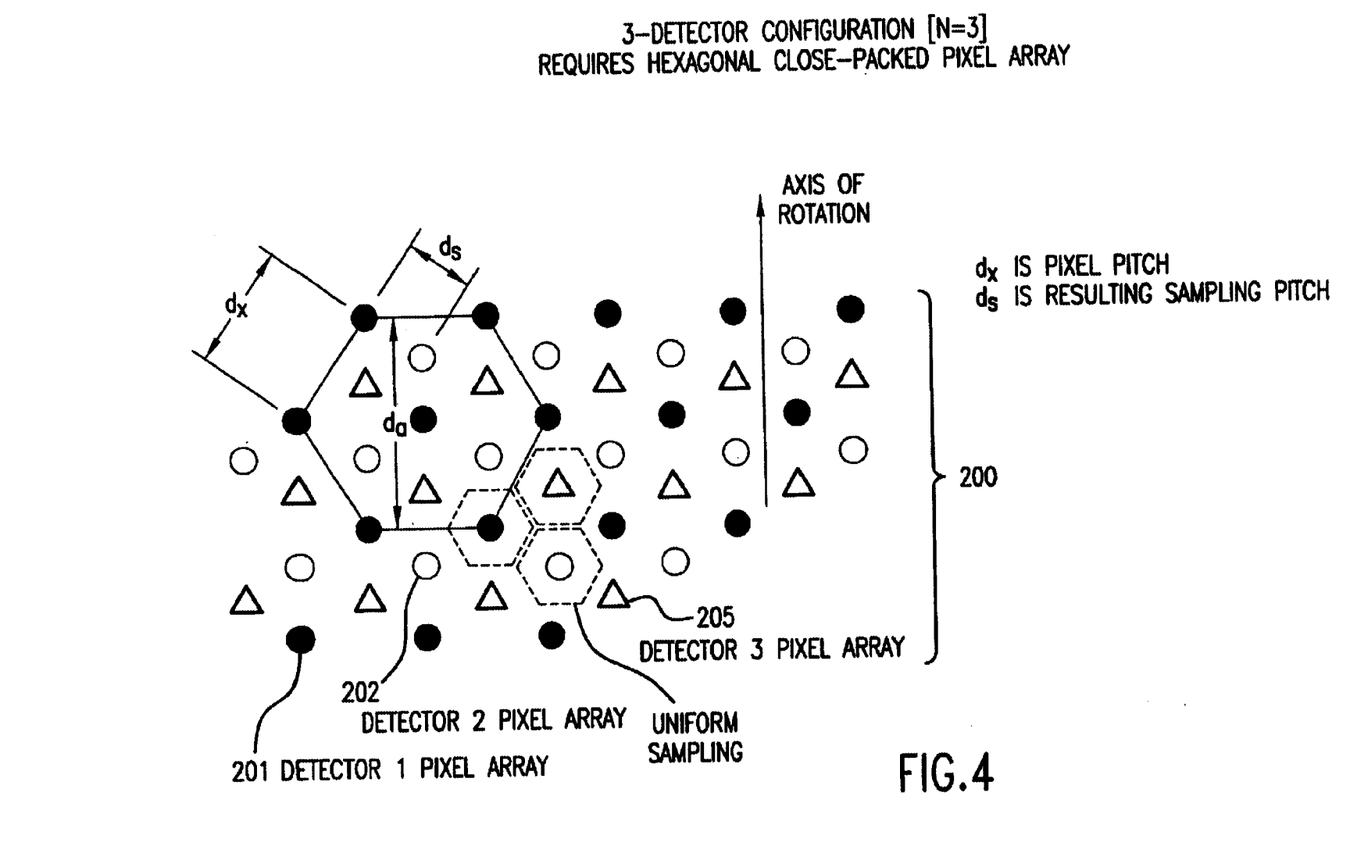

In one embodiment illustrated in FIG. 4, the imager has a three-detector configuration that can be applied to either a homogeneous detector with a hexagonal sparse hole collimator array or a pixellated detector with hexagonal close-packing of the pixels. More specifically, FIG. 4 illustrates a top view of a 3-head planar image sampling 200 which is obtained by the combination of acquired image data from the three detectors after each of the detectors has spent time at the projection under consideration. The black circles 201 represent the pixel array data acquired by a first detector. The black circles 201 represent the position of the collimator apertures and indicate that the pattern of the collimator apertures is also hexagonally close-packed. However, the detector apertures can be made to have any shape, such as hexagonal, circular, square, etc., as long as the apertures assume the hexagonal close-packed array pattern. The white circles 202 represent the data acquired by a second detector. Note that the second detector has been aligned so that it is offset in both the axial and the transaxial directions compared with the first detector. The triangles 205 represent the data acquired by a third detector. Again, the third detector has been strategically aligned to be offset from, and complementary to, the data from the first and second detectors. For homogeneous detectors, such as those using NaI crystals, the collimator hole patterns for each detector are sparsely separated so that the separate detectors are separated by sufficient distances as needed for sparse hole imaging. For pixellated detectors, such as those with CZT crystals, the hole patterns are registered to each pixel.

Figure 3:
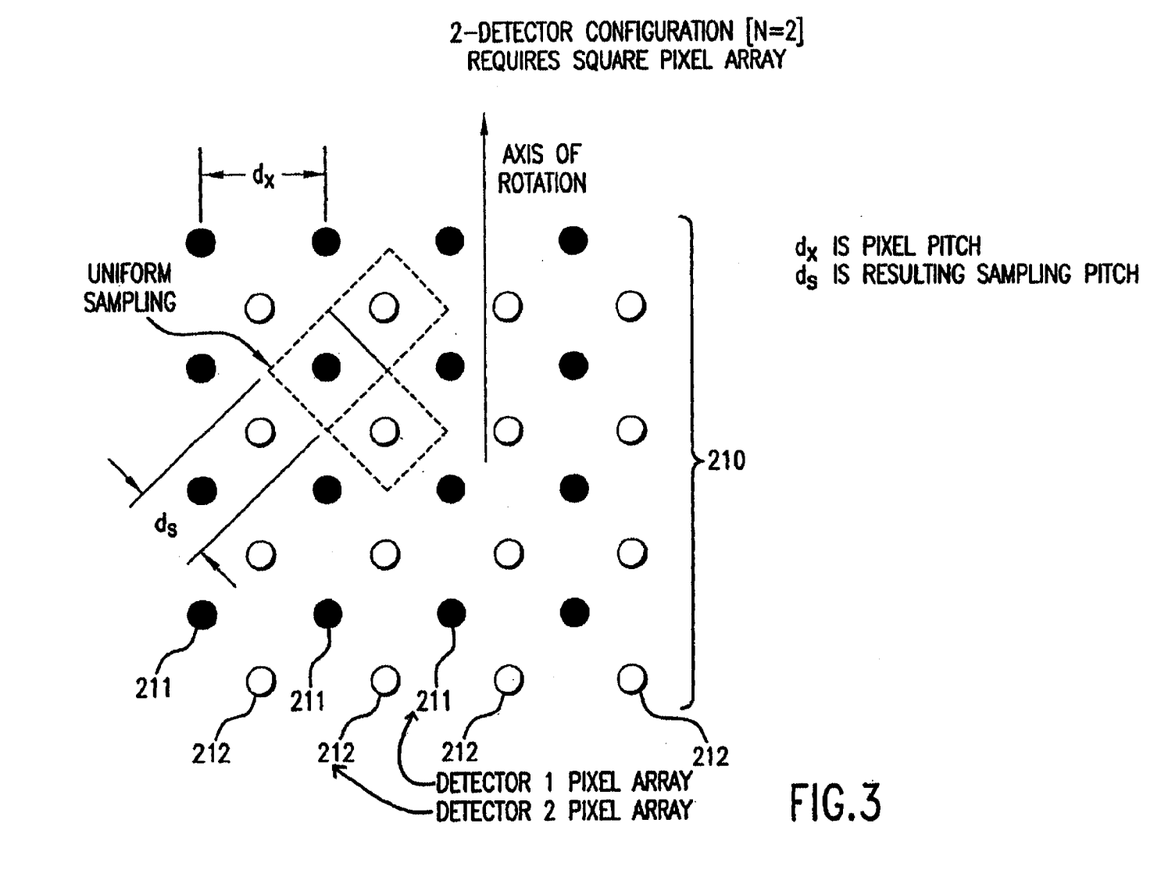
FIGS. 3–5 are top-views of planar image samplings that are achieved through multiple detectors after each of the detectors has spent time at the projection under consideration in accordance with embodiments of the present invention.

FIG. 3 illustrates a two-detector configuration in which the sample area is divided into squares. In particular, FIG. 3 illustrates a top view of two-detector planar image sampling 210 which is achieved by the combination of the two detectors after each of the detectors has spent time at the projection under consideration. The black circles 211 represent the data sampled by a first detector (Detector 1), and the white circles 212 represent the data sampled by a second detector (Detector 2). As with sample 200 in FIG. 4, the arrays 211 and 212 also represent the locations of the apertures for the detectors, but the apertures themselves can assume any shape as long as the detector pixel packing pattern is a square array.

Figure 5:
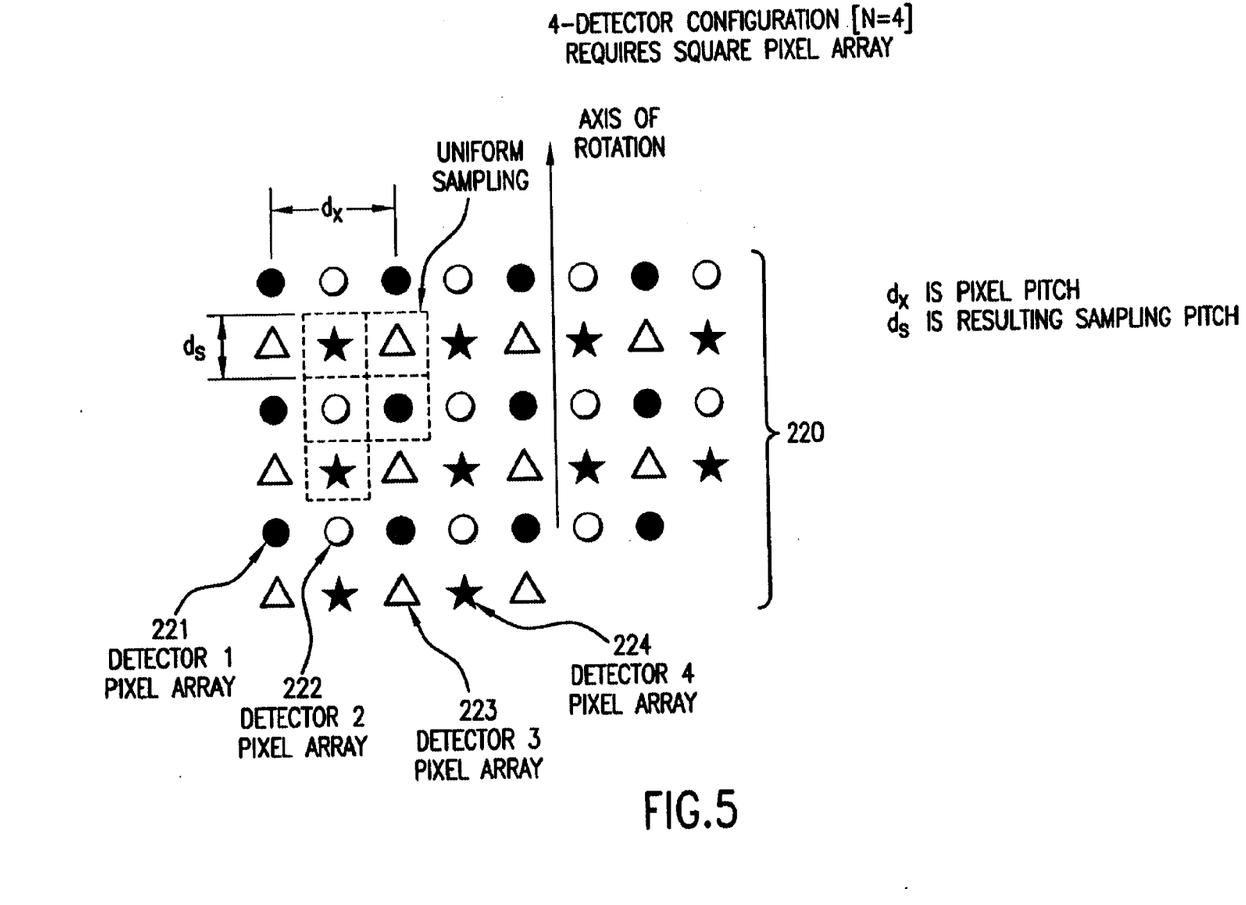
Figure 6A:
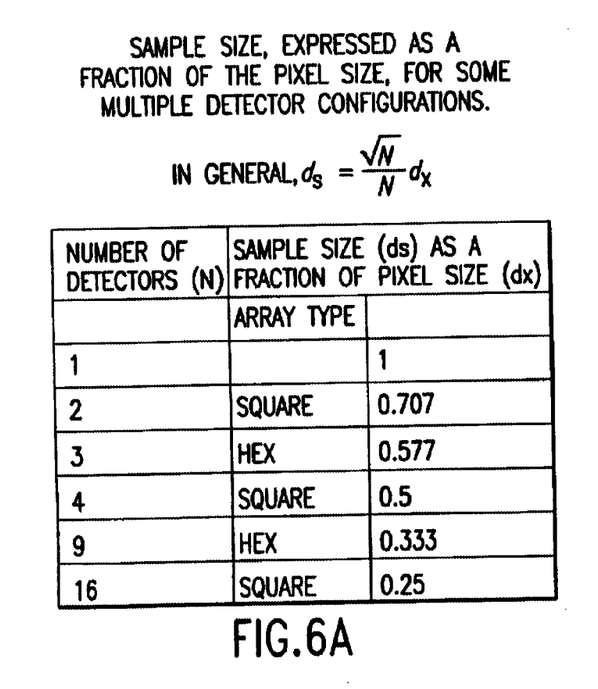
FIG. 6A is a table and FIG. 6B is a graph, showing the general relationship between sample pitch (as a fraction of pixel pitch) and the number of detectors.
Figure 6B:
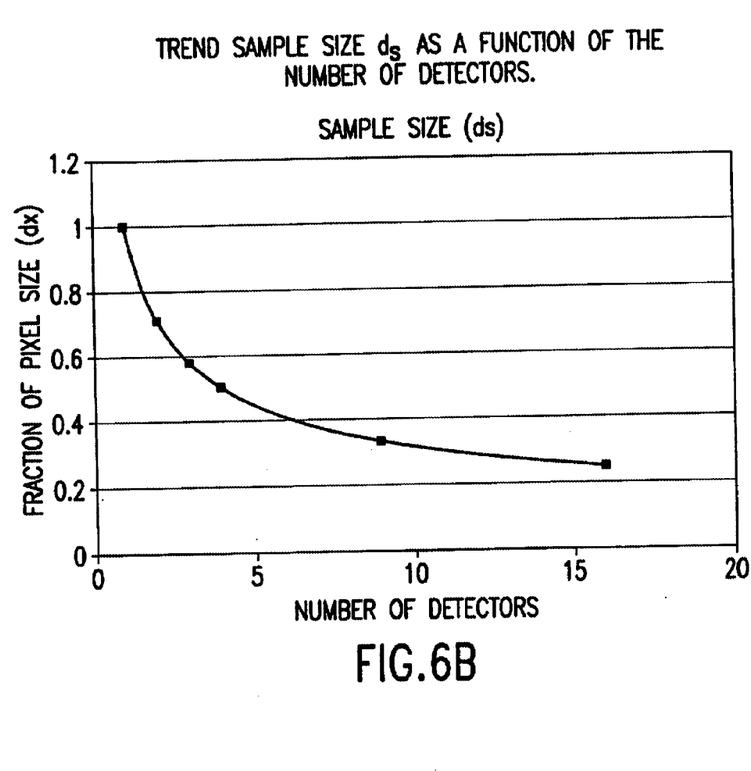

An analogous four-detector system can be formed by duplicating the sampling configuration of the first and second detector with another pair of the similarly positioned detectors. This configuration is illustrated by FIG. 5, which is a top-view of a first 4-head planar image sampling 220 achieved by the four detectors after each of the detectors has spent time at the projection under consideration. The black circles 221, white circles 222, triangles 223 and stars 224 respectively represent the data sampled by the first, second, third, and fourth detectors. The equation in the table of FIG. 6A shows that a 4-headed system will have a smaller sample size of 0.5 times the pixel pitch as compared with the 2-headed system, which has a sample size o 0.707 times the pixel pitch. FIG. 6B shows the trend of sample size as a function of the number of detectors in the system. Additionally, the 4-headed system will acquire twice the amount of counts as the 2-headed system for the same time period.

Figure 7A:
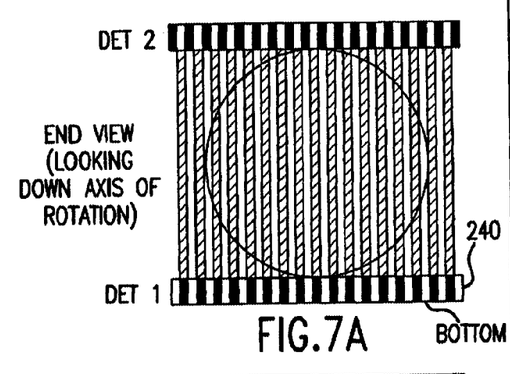
FIGS. 7A–7B and FIGS. 8A–8C are end views looking down the axis of rotation for the detectors during SPECT with configurations having, respectively, two detectors and three detectors in accordance with embodiments of the present invention.
Figure 7B:
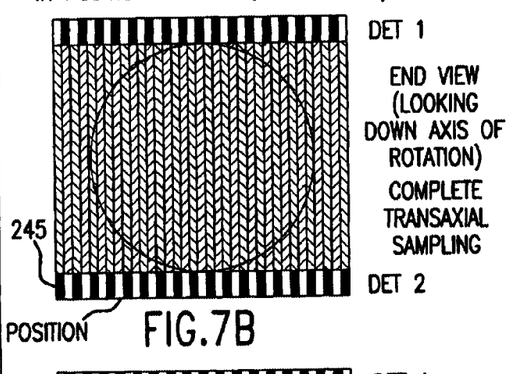
Figure 7C:
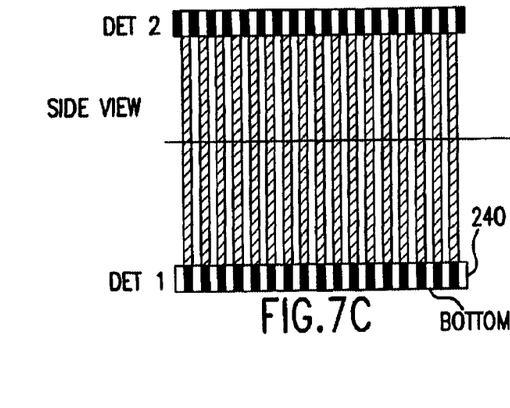
FIGS. 7C–7D and 8D–8F are side views along the axis of rotation for the detectors during SPECT with configurations having, respectively, two detectors and three detectors in accordance with embodiments of the present invention.
Figure 7D:
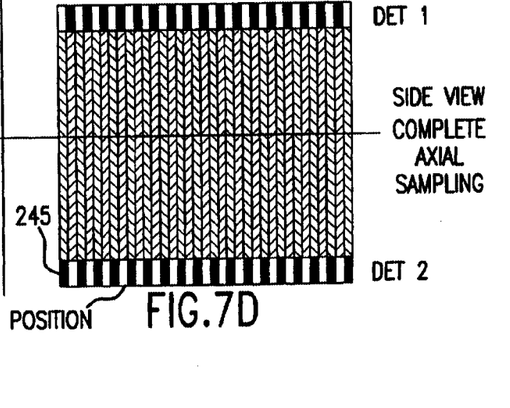

As described above, the radionuclide imager of the present invention accomplishes a complete scan of the target through strategic placement of the detectors relative to each other during SPECT scanning. FIGS. 7A–7D schematically illustrate how a radionuclide imager having two detectors produces a complete image sampling, such as the one illustrated in FIG. 3, to acquire complete data sets for the target even though each of the individual collimated detectors only detects samples from a portion of the target. For ease of description, FIGS. 7A–7D illustrate how the radionuclide imager acquires complete data sets for the detector-at-the-bottom projection, but it should be appreciated that complete data sets are acquired completely around the target in the axial and transaxial directions. In particular, a first detector 240 and a second detector 245 are shown having shaded and clear sections, where the counts are acquired in only the shaded regions, as described above. FIGS. 7A–7B illustrate how a target is completely sampled in the transaxial direction, and FIGS. 7C–7D illustrate how a target is completely sampled in the axial direction. In FIGS. 7A and 7C, the first detector 240 is positioned in the bottom position, acquiring half of the necessary data in both transaxial and axial directions. In FIGS. 7B and 7D, the second detector 245 is shown in the bottom position, acquiring the complementary half of the projection data that was not originally acquired by the first detector 240.

Figure 8A:
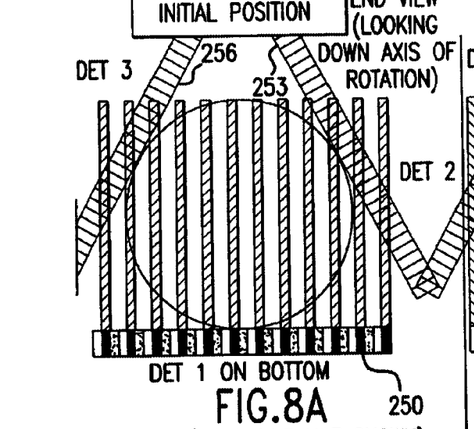
Figure 8B:
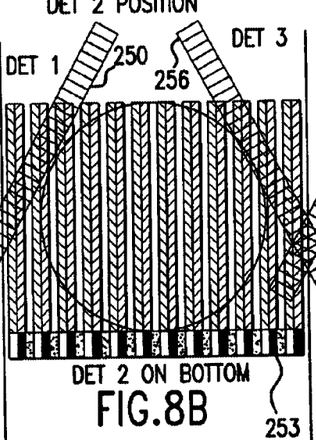
Figure 8C:
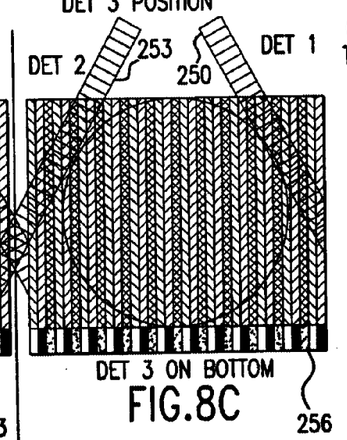
Figure 8D:
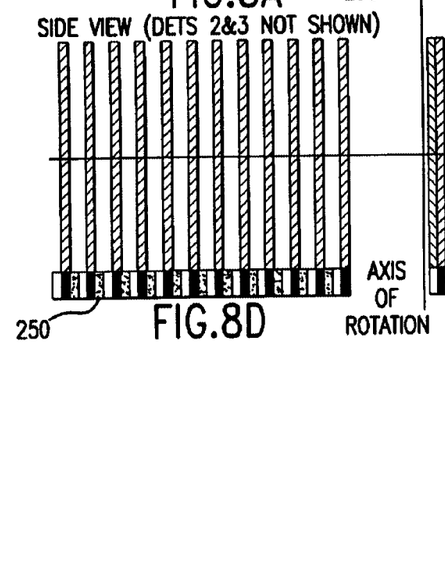
Figure 8E:
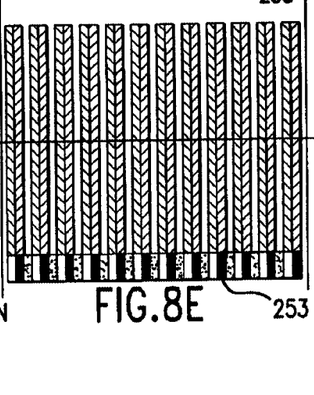
Figure 8F:
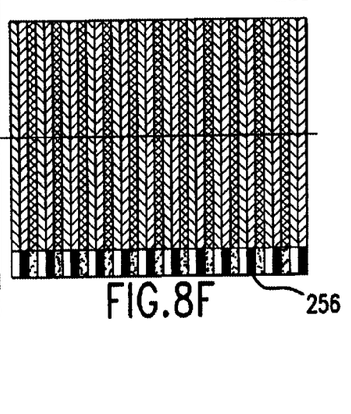

Likewise, FIGS. 8A–8F illustrate the corresponding schematic representation of SPECT scanning with the three-detector configuration of FIG. 4 to acquire complete data sets for the target even though each of the individual collimated detectors only detects samples from a portion of the target. Again, FIGS. 8A–8F illustrate how the radionuclide imager acquires complete data sets for the detector-at-the-bottom projection, but it should be appreciated that complete data sets are acquired completely around the target in both transaxial and axial directions. A primary collimated detector 250 actively scans in the black shaded areas, a secondary collimated detector 253 actively scans in the grey shaded areas, and a tertiary collimated detector 256 actively scans in the unshaded areas. FIGS. 8A–8C illustrate how a target is completely sampled in the transaxial direction, and FIGS. 8D–8F illustrate how a target is completely sampled in the axial direction. In FIGS. 8A and 8D, the primary detector 250 is positioned in the bottom projection, acquiring data in both transaxial and axial directions. In FIGS. 8B and 8E, the secondary detector 253 is shown in the bottom projection, acquiring a portion of the projection data that was not originally acquired by the primary detector 250. Then, in FIGS. 8C and 8F, the tertiary detector 256 is shown in the bottom projection, acquiring a complementary portion of the projection data that was not originally acquired by either the primary detector 250 or the secondary detector 253.

It should be appreciated that the operation of SPECT scanning with a 4-head detector configuration to produce the samplings, such as FIG. 5, is not described herein, but the complementary data acquisition concept described above in FIGS. 7 and 8 can be easily extended to 4-head detectors according the current invention. Likewise, it should be similarly appreciated that imagers having more than four detectors can be formed applying the same principle of performing SPECT scanning with the strategic placement of the detector heads relative to each other such that for any given projection which is to be acquired, a complete high resolution imaging of the projection is acquired by summing the complementary contributions of the multiple detector heads. By increasing the number of detectors, the imager can achieve higher sub-intrinsic resolution as shown by the equation in FIG. 6A. Furthermore, the number of lower-resolution, higher sensitivity possibilities also increases as the number of heads is increased. For example, four detectors can be arranged to be two identical 2-head systems, thereby doubling the sensitivity with a coarser resolution.

Figure 9:
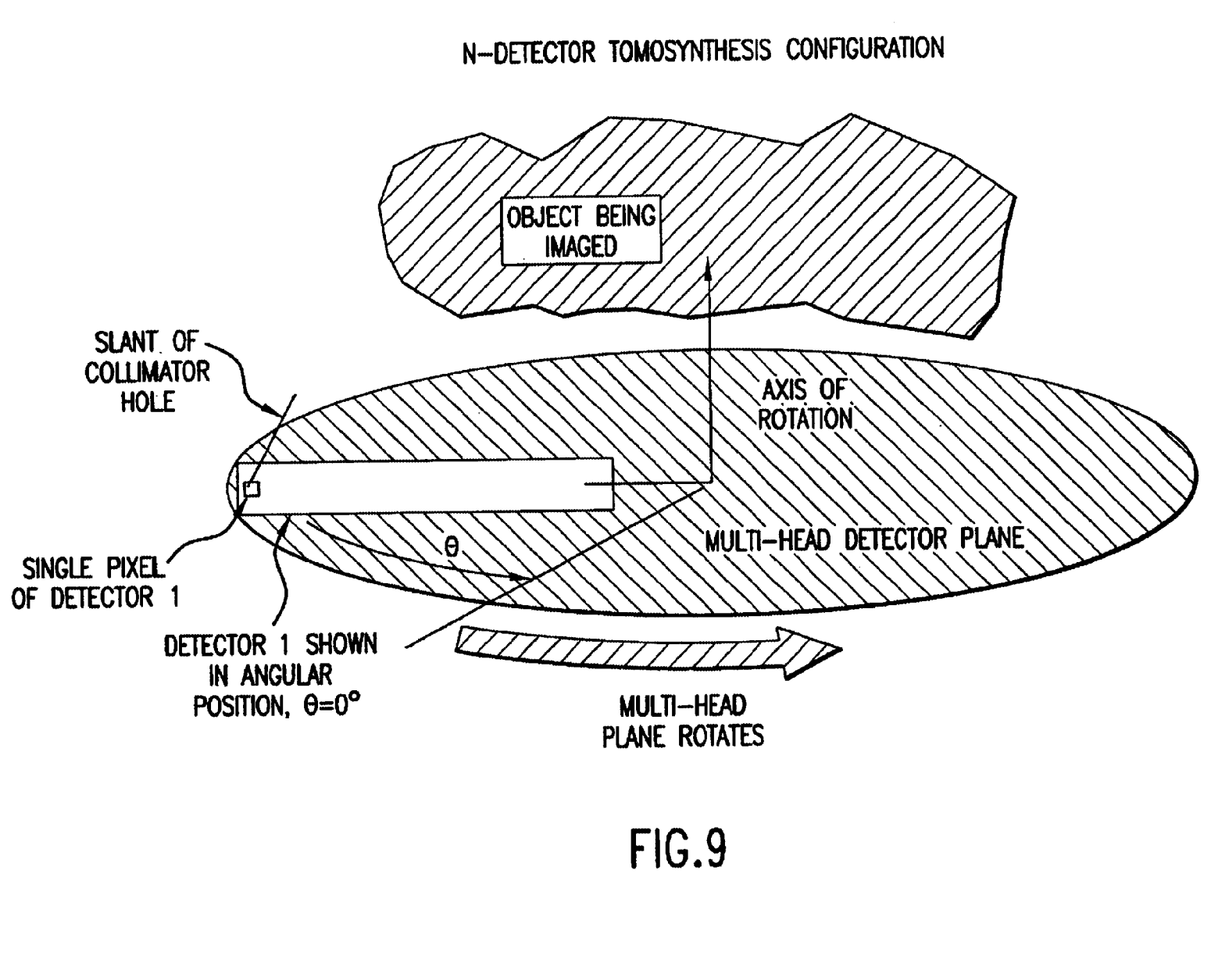
FIG. 9 is a diagram showing the orientation of a detector head and the slant angle of a collimator hole with respect to an object being imaged and the direction of rotation of the detector head with respect to the object and the slant angle of the collimator hole, according to an embodiment of the invention.

FIG. 9 shows a configuration of another form of tomographic data acquisition in nuclear medicine, known as tomosynthesis or ectomography. This technique is described in Dale, Susanne M. et al., "Comparison of SPECT and Ectomography for Evaluating Myocardial Perfusion with Technetium-99m Setamibi, Journal of Nuclear Medicine Vol. 38:754–59 (1997), incorporated herein by reference.

Tomosynthesis involves the use of a slant-hole collimator and a rotating detector plane parallel to the patient or object to be imaged, such that a partial tomographic sampling of the patient or object to be imaged is obtained. If multiple detectors are positioned on the detector plane, each with the same slant-hole collimator, then the strategic positioning of the pixel arrays of the detectors on the detector plane according to the precepts of the invention can be made to achieve the same complementary sub-pixel sampling resolution as in the complete orbit (i.e., circular) tomographic acquisition described above. As with the complete orbit SPECT acquisition, a complete rotation of such multiple detectors in the tomographic plane is sufficient to acquire a complement of sub-pixel samples.

While the invention has been described with reference to the structures disclosed herein, it is not confined to the details set forth. Instead, this application is intended to cover any such modifications or changes as may be apparent to those skilled in the art from the foregoing disclosure within the scope of the following claims.

What is claimed is:

1. A radionuclide imaging device, comprising:
    a plurality of radiation detectors for scanning a target, each radiation detector including a collimator having a pattern of apertures that is offset from collimator aperture patterns of others of said plurality of radiation detectors, such that for a particular target projection sampling to be acquired, each of the radiation detectors provides a complementary image sampling contribution at said particular projection, said complementary image sampling contributions being summed to provide a complete sampling of the target at said particular projection.

2. The radionuclide imaging device of claim 1, wherein each of said radiation detectors is a homogenous area detector, and said plurality of radiation detectors are rotated around said target such that each detector scans the same target projection at different times.

3. The radionuclide imaging device of claim 2, wherein each of said radiation detectors uses sparse hole sampling, and motion required for the sparse hole sampling is provided by said radiation detectors' rotation around the target.

4. The radionuclide imaging device of claim 1, wherein each of said radiation detectors is a pixellated detector, and said plurality of radiation detectors are rotated around said target such that each detector scans the same target projection at different times.

5. The radionuclide imaging device of claim 4, wherein each of said radiation detectors uses registered collimator sampling, and motion required for registered collimator sampling is provided by said radiation detectors' rotation around the target.

6. The radionuclide imaging device of claim 1, wherein the collimator aperture pattern of each of said radiation detectors is offset in both an axial and a transaxial direction from the collimator aperture patterns of the other radiation detectors of the plurality of radiation detectors.

7. A radionuclide imaging device comprising an array of radiation detectors arranged on a plane parallel to a target to be imaged, wherein each of said radiation detectors is configured with a slant-hole collimator and is rotated in said plane for performing tomosynthesis tomography of said target, and
    wherein each of said slant-hole collimators of said radiation detectors has a slant-hole angle different from slant-hole angles of the others of said plurality of radiation detectors, such that for a particular target projection sampling to be acquired by a rotation of said detectors around said plane, each of the radiation detectors provides a complementary contribution at the projection which are summed to provide a complete sampling of the target projection.

8. The radionuclide imaging device of claim 7, wherein each of said radiation detectors is a homogenous area detector.

9. The radionuclide imaging device of claim 8, wherein each of said radiation detectors uses sparse hole sampling, and motion required for the sparse hole sampling is provided by said radiation detectors' rotation in said plane.

10. The radionuclide imaging device of claim 7, wherein each of said radiation detectors is a pixellated detector.

11. The radionuclide imaging device of claim 10, wherein each of said radiation detectors uses registered collimator sampling, and motion required for registered collimator sampling is provided by said radiation detectors' rotation in said plane.

12. A method of acquiring at a particular projection a planar image of an object emitting radionuclide radiation, comprising the steps of:
    sequentially imaging said projection with a plurality of radiation detectors each including a collimator having a pattern of apertures that is offset from collimator aperture patterns of others of said plurality of radiation detectors, such that for a particular target projection sampling to be acquired, each of the radiation detectors provides a complementary image sampling contribution at said particular projection; and
    summing said complementary image sampling contributions to provide a complete sampling of the target at said particular projection.

13. The method of claim 12, further comprising the steps of imaging said object at multiple projections using said steps of sequential imaging and summing, by rotating said plurality of radiation detectors around said object, and combining image sampling at each of said multiple projections to obtain a tomographic image of said object.

14. A radiation detector for use in a radionuclide imaging device having a plurality n of radiation detectors for obtaining tomographic images of a target, said radiation including a collimator having a number of apertures equal to 1/n of the total number of apertures required to acquire complete image sampling data at a particular target projection.

15. A radiation detector as set forth in claim 14, wherein a pattern of said apertures of said collimator is offset from collimator aperture patterns of others of said plurality n of radiation detectors used in said radionuclide imaging device.

* * * * *